United States Patent
Ferrari et al.

(10) Patent No.: US 9,206,220 B2
(45) Date of Patent: Dec. 8, 2015

(54) PROCESS FOR PREPARING HIGH PURITY URSODEOXYCHOLIC ACID

(71) Applicant: ERREGIERRE S.P.A., San Paolo d'Argon (IT)

(72) Inventors: Massimo Ferrari, Cenate Sotto (IT); Fabrizio Zinetti, Casazza (IT)

(73) Assignee: Erregierre S.p.A., San Paolo d'Argon (IT)

(*) Notice: Subject to any disclaimer, the term of this patent is extended or adjusted under 35 U.S.C. 154(b) by 0 days.

(21) Appl. No.: 14/418,296

(22) PCT Filed: Jul. 30, 2013

(86) PCT No.: PCT/EP2013/066002
§ 371 (c)(1),
(2) Date: Jan. 29, 2015

(87) PCT Pub. No.: WO2014/020024
PCT Pub. Date: Feb. 6, 2014

(65) Prior Publication Data
US 2015/0291651 A1   Oct. 15, 2015

(30) Foreign Application Priority Data
Jul. 31, 2012   (IT) .............................. MI2012A1344

(51) Int. Cl.
*C07J 9/00* (2006.01)
*C07J 75/00* (2006.01)

(52) U.S. Cl.
CPC . *C07J 9/005* (2013.01); *C07J 75/00* (2013.01)

(58) Field of Classification Search
CPC .................................. C07J 9/005; C07J 75/00
See application file for complete search history.

(56) References Cited

PUBLICATIONS

Giovannini et al, Steroids, 7 alpha- and 12 alpha -Hydroxysteroid Dehydrogenases from Acinetobacter calcoaceticus lwoffiii: a New Integrated Chemo-enzymatic Route to Ursodeoxycholic Acid, 2008, 73, pp. 1385-1390.*
International Search Report dated Nov. 27, 2013 corresponding to International Patent Application No. PCT/EP2013/066002; 3 pages.
Written Opinion dated Nov. 27, 2013 corresponding to International Patent Application No. PCT/EP2013/066002; 6 pages.
Takashi Iida et al.; "Potential bile acid metabolites. 6.Stereoisomeric 3,7-dihydroxy-5.beta.-cholanic acids", The Journal of Organic Chemistry, 1982, 47, 2966-2972.
Giovannini P P et al.; "7alpha- and 12alpha-Hydroxysteroid dehydrogenases from Acinetobacter calcoaceticus lwoffii,: A new integrated chemo-enzymatic route to ursodeoxycholic acid," Steroids, Elsevier Science Publishers, New York, NY, US, vol. 73, No. 14, (Dec. 22, 2008), pp. 1385-1390.

* cited by examiner

*Primary Examiner* — Paul A Zucker
(74) *Attorney, Agent, or Firm* — Ohlandt, Greeley, Ruggiero & Perle, L.L.P.

(57) ABSTRACT

The present invention describes a process for the synthesis of ursodeoxycholic acid wherein the purification of the crude ursodeoxycholic acid (containing approximately 13-15% of chenodeoxycholic acid impurity) takes place first passing through a salification with imidazole and a subsequent purification via "methyl ester", which allows a finished product with an extremely low content of known "cheno and "litho" impurities to be obtained. The present invention also describes the recovery steps of cholic acid and 3α-hydroxy-7-ketocholanic acid from the mother liquors of process intermediates.

12 Claims, No Drawings

PROCESS FOR PREPARING HIGH PURITY URSODEOXYCHOLIC ACID

FIELD OF THE INVENTION

The present invention relates to a process for preparing high purity ursodeoxycholic acid.

The present invention originates in the pharmaceutical sector and specifically in the field of chemical processes for preparing active ingredients.

BACKGROUND OF THE INVENTION

Due to its many functions, ursodeoxycholic acid is an active ingredient of considerable interest in human therapy; it, for example, promotes the dissolution of gallstones, lowers the percentage of cholesterol in the blood, and blood sugar and is also used as a diuretic and as fat metabolism accelerator.

There are several known processes for preparing ursodeoxycholic acid. All the known processes have the disadvantage of leading to the production of a mixture of ursodeoxycholic, chenodeoxycholic, lithocholic, cholic and isourso in variable amounts from process to process.

There are various methods of purifying ursodeoxycholic acid from the above-mentioned components.

There however continues to be a need to have available a process for preparing high purity ursodeoxycholic acid, the costs of which are as contained as possible.

SUMMARY OF THE INVENTION

The present invention overcomes the above-mentioned problems by means of a process for the synthesis of ursodeoxycholic acid, said process comprising the following steps:

(I) preparing methyl $3\alpha,7\alpha$-diacetoxy-$12\alpha$-hydroxycholanate through the esterification of cholic acid to obtain the methyl cholate intermediate which is not isolated and is acetylated in position 3 and 7 to obtain the methyl $3\alpha,7\alpha$-diacetoxy-$12\alpha$-hydroxycholanate intermediate which is isolated by crystallisation;

(II) preparing methyl $3\alpha,7\alpha$-diacetoxy-12-ketocholanate through oxidisation of the methyl $3\alpha,7\alpha$-diacetoxy-$12\alpha$-hydroxycholanate intermediate on the hydroxyl group in position 12 to give the methyl $3\alpha,7\alpha$-diacetoxy-12-ketocholanate intermediate which is isolated by crystallisation;

(III) preparing the crude chenodeoxycholic acid through Wolff-Kishner reduction of the ketone group in position 12 of the methyl $3\alpha,7\alpha$-diacetoxy-12-ketocholanate intermediate, and concomitant reacting by means of hydrolysis the ester groups in position 3,7 and 24; to obtain the crude chenodeoxycholic acid;

(IV) preparing the $3\alpha$-hydroxy-7-ketocholanic acid through oxidisation of the hydroxyl group in position 7 present on the crude chenodeoxycholic acid intermediate, to give $3\alpha$-hydroxy-7-ketocholanic acid;

(V) preparing the ursodeoxycholic acid imidazole salt through reduction of the ketone group present in position 7 of the $3\alpha$-hydroxy-7-ketocholanic acid intermediate to give the crude ursodeoxycholic acid in the form of a mixture of ursodeoxycholic acid and chenodeoxycholic acid then treating with imidazole to give the ursodeoxycholic acid imidazole salt which is isolated by crystallisation;

(VI) preparing the ursodeoxycholic acid methyl ester through esterification of the ursodeoxycholic acid imidazole salt intermediate to give the ursodeoxycholic acid methyl ester which is isolated by crystallisation;

(VII) preparing the ursodeoxycholic acid by means of hydrolysis of the ursodeoxycholic acid methyl ester intermediate, and then acidifying to give the ursodeoxycholic acid.

Surprisingly, the final step (i.e. steps V-VII) of the purification of the crude ursodeoxycholic acid (containing, after the reduction of step V, around 13-15% of chenodeoxycholic acid impurity), passing first through a salification with imidazole and a subsequent purification via "methyl ester", allows a finished product having an extremely low content of impurities known as "cheno" (less than 0.35%), "litho" (less than 0.05%), "cholic" (less than 0.1%) and "isourso" (less than 0.05%) to be obtained.

For these impurities, the official monographs (USP and Ph. Eur.) allow the following impurity contents: "cheno" less than 1.5% (USP), "litho" less than 0.1% (Ph. Eur.) "cholic" less than 0.5% (Ph. Eur.) and "iso-urso" less than 0.1% (Ph. Eur.). Details and further advantages of the present invention are described below.

DETAILED DESCRIPTION OF THE INVENTION

In one preferred aspect, the present invention relates to a process, as described above, comprising a recovery step (VIII) of the cholic acid, wherein the crystallisation mother liquors from steps (I) and (II) are conveniently stored, combined and subjected to a recovery step of the cholic acid by means of a reduction reaction, preferably with sodium borohydride in a basic environment, and subsequent basic treatment, preferably with sodium hydrate, and acidification, preferably with phosphoric acid, to obtain a certain quantity of recovered cholic acid corresponding to about 20-30% of the starting cholic acid used in step (I).

This quantity of cholic acid recovered as described above can be used in subsequent production cycles thus significantly reducing production costs and obtaining overall returns of the first two steps greater than 90%.

In another preferred aspect, the present invention relates to a process, as described above, comprising a recovery step (IX) of the $3\alpha$-hydroxy-7-ketocholanic acid, wherein the crystallisation mother liquors from steps (V) and (VI) are stored and the mother liquors from step (VI), after distillation of the solvent (ethyl acetate), are subjected to a basic treatment, preferably in water with an alkaline hydrate such as sodium hydrate and then combined with the mother liquors from step (V) to obtain a mixture which, after acidification, is subjected to oxidation, preferably for treatment with sodium bromate in the presence of sodium bromide in an acid environment in order to obtain a certain amount of $3\alpha$-hydroxy-7-ketocholanic acid corresponding to about 20-30% of the starting $3\alpha$-hydroxy-7-ketocholanic acid used in step (V).

This amount of $3\alpha$-hydroxy-7-ketocholanic acid recovered as described above can be used in subsequent production cycles significantly reducing production costs and obtaining overall returns of the last 4 steps greater than 85%.

In one particularly preferred manner, the process of the invention thus comprises both recovery step (VIII) of the cholic acid, as described above, and recovery step (IX) of the $3\alpha$-hydroxy-7-ketocholanic acid, as described above.

Step (I) preferably takes place according to the following scheme:

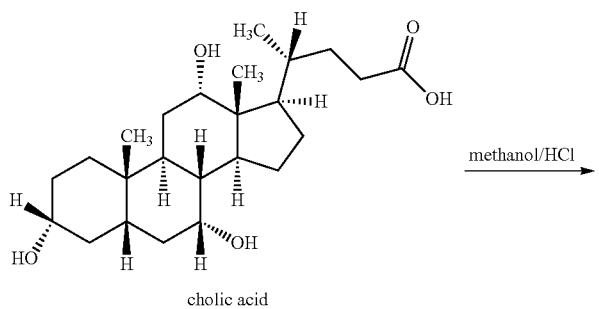

cholic acid

Molecular Weight = 408,58
Molecular Formula = C24H40O5

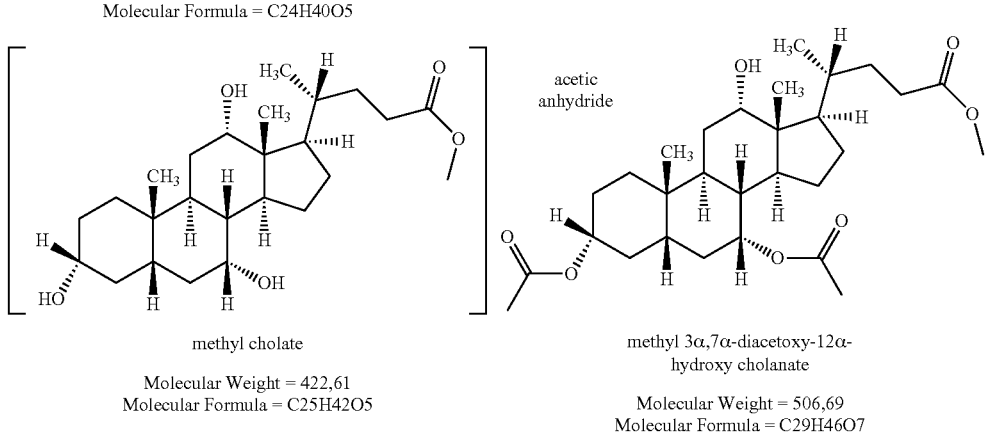

methyl cholate

Molecular Weight = 422,61
Molecular Formula = C25H42O5 methyl 3α,7α-diacetoxy-12α-hydroxy cholanate

Molecular Weight = 506,69
Molecular Formula = C29H46O7 wherein the esterification reaction of the cholic acid takes place by means of the methanol, catalysed by the hydrochloric acid, to give the intermediate non-isolated filtered methyl intermediate; which is acetylated in position 3 and 7 with acetic anhydride, in the presence of the 4-dimethylaminopyridine catalyst, to give the methyl 3α,7α-diacetoxy-12α-hydroxycholanate intermediate.

Step (II) preferably takes place according to the following scheme:

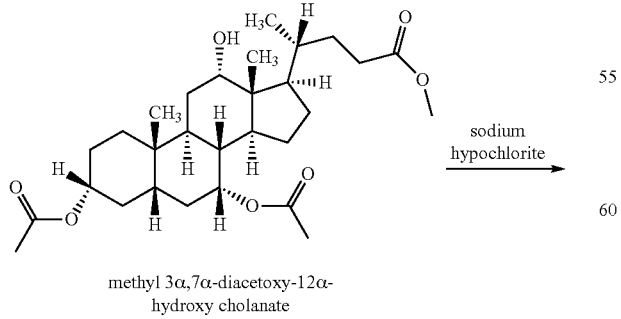

methyl 3α,7α-diacetoxy-12α-hydroxy cholanate

Molecular Weight = 506,69
Molecular Formula = C29H46O7

-continued

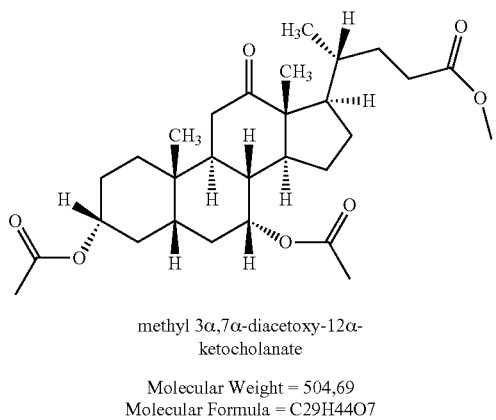

methyl 3α,7α-diacetoxy-12α-ketocholanate

Molecular Weight = 504,69
Molecular Formula = C29H44O7 wherein the oxidation reaction of the methyl 3α,7α-diacetoxy-12α-hydroxycholanate intermediate on the hydroxyl group in position 12, takes place by means of the sodium hypochlorite, to give the methyl 3α,7α-diacetoxy-12-ketocholanate intermediate.

Step (III) preferably takes place according to the following scheme:

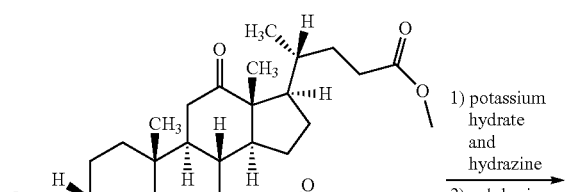

methyl 3α,7α-diacetoxy-12α-
hydroxy cholanate

Molecular Weight = 504,67
Molecular Formula = C29H44O7

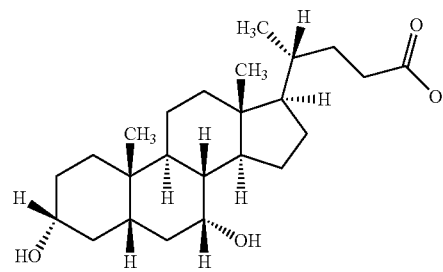

crude chenodeoxycholic acid

Molecular Weight = 392,58
Molecular Formula = C24H40O4 wherein the Wolff-Kishner reduction reaction of the ketone group in position 12 of the methyl 3α,7α-diacetoxy-12-ketocholanate intermediate, and wherein the hydrolysis reaction of the ester groups in position 3,7 and 24, is advantageously carried out in the presence of potassium hydroxide and hydrazine; the crude chenodeoxycholic acid is obtained by subsequent treatment with sulphuric acid (neutralisation).

Step (IV) preferably takes place according to the following scheme:

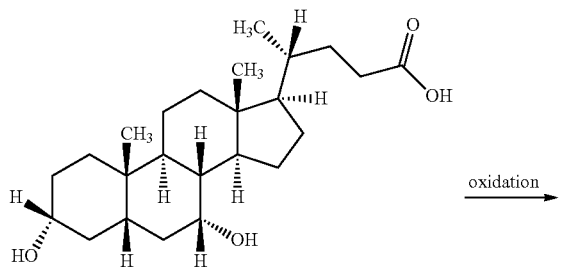

crude chenodeoxycholic acid

Molecular Weight = 392,58
Molecular Formula = C24H40O4

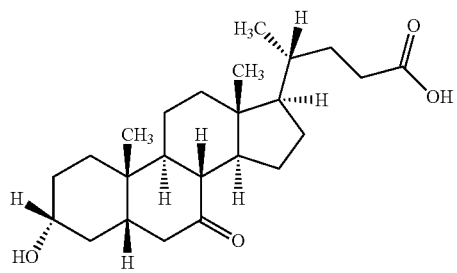

3α-hydroxy-7-ketocholanic acid

Molecular Weight = 390,57
Molecular Formula = C24H38O4 wherein the oxidation reaction of the hydroxyl group in position 7 present on the intermediate chenodeoxycholic acid takes place by means of treatment with sodium bromate in the presence of sodium bromide in an acid environment, which is rendered acid preferably by sulphuric acid.

Step (V) preferably takes place according to the following scheme

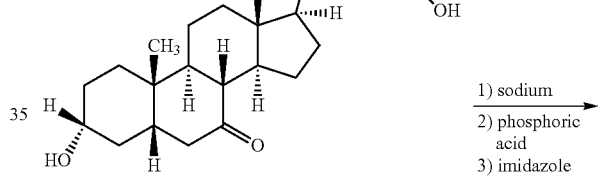

3α-hydroxy-7-ketocholanic acid

Molecular Weight = 390,57
Molecular Formula = C24H38O4

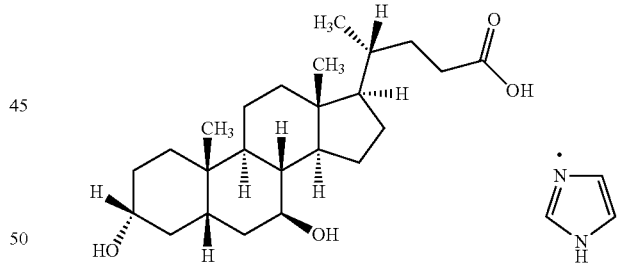

ursodeoxycholic acid imidazole salt

Molecular Weight = 392,58 68,08
Molecular Formula = C24H40O4•C3H4N2 wherein the reduction of the ketone group present in position 7 of the 3α-hydroxy-7-ketocholanic acid intermediate takes place by means of the metallic sodium to give the crude ursodeoxycholic acid (mixture of ursodeoxycholic acid and chenodeoxycholic acid), followed by successive treatment with imidazole to give the ursodeoxycholic acid imidazole salt.

Step (VI) preferably takes place according to the following scheme:

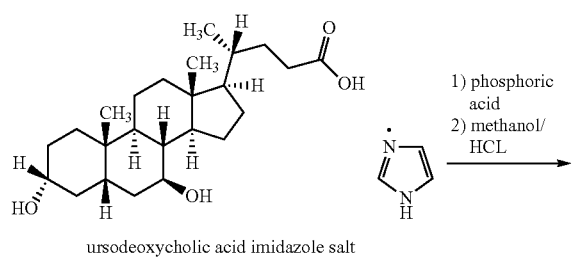
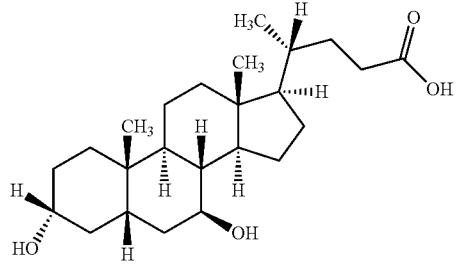

ursodeoxycholic acid imidazole salt

Molecular Weight = 392,58 68,08
Molecular Formula = C24H40O4·C3H4N2

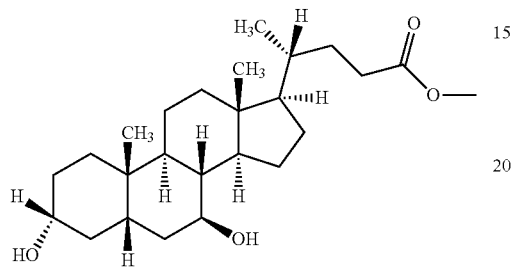

ursodeoxycholic acid methyl ester

Molecular Weight = 406,61
Molecular Formula = C25H42O4 wherein the esterification reaction of the intermediate ursodeoxycholic acid imidazole salt takes place after acidification of the imidazole salt with phosphoric acid and successive esterification by means of the methanol in the presence of acid catalysis (preferably by hydrochloric acid), to give the ursodeoxycholic acid methyl ester.

Step VII preferably takes place according to the following scheme:

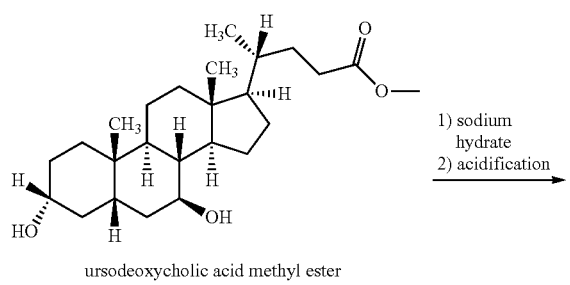

ursodeoxycholic acid methyl ester

Molecular Weight = 406,61
Molecular Formula = C25H42O4 ursodeoxycholic acid

Molecular Weight = 392,58
Molecular Formula = C24H40O4 wherein the hydrolysis reaction of the ursodeoxycholic acid methyl ester intermediate takes place by means of the sodium hydroxide and the subsequent acidification takes place with acetic acid and phosphoric acid to give the ursodeoxycholic acid.

The present invention will now be illustrated with reference to the following examples, which are provided for illustrative purposes only and are not to be construed as limiting of the scope of protection as is defined in the accompanying claims.

EXAMPLE 1

Step I: Preparation of methyl 3α,7α-diacetoxy-12α-hydroxycholanate

1200 Kg of methyl alcohol, 750 Kg of cholic acid and 7.5 Kg of hydrochloric acid 37% were loaded into a reactor. The temperature of the mixture was brought to boiling and allowed to reflux for 1 hour, then 9.9 Kg of sodium acetate were added. The methyl alcohol was distilled until a paste-like residue was obtained, then 1250 Kg of toluene and 22.5 Kg of 4-dimethylaminopyridine were added, the mass was at the temperature of about 20° C., then 449 Kg of acetic anhydride were added and the mass was maintained at about 20° C. for 10 hours, then 450 Kg of deionised water were added.

The mass was heated to around 50° C. and, at this temperature, the phases were separated and the aqueous phase was eliminated.

The organic phase was subjected to vacuum distillation until a dense mass was obtained. 1125 Kg of ethyl acetate were added to the residue. The mass was heated to about 50° C. until complete dissolution.

The solution was cooled to a temperature of −10°/−5° C. at which precipitation of the product took place. The suspension was centrifuged and the solid residue washed with 250 Kg of ethyl acetate.

The centrifugal mother liquors were stored for use in the recovery step of the cholic acid as detailed below in the example 8.

All the wet product obtained (methyl 3α,7α-diacetoxy-12α-hydroxycholanate) was used in the subsequent step

EXAMPLE 2

Step II: Preparation of methyl 3α,7α-diacetoxy-12-ketocholanate

1125 Kg of ethyl acetate, the entire amount of methyl 3α,7α-diacetoxy-12α-hydroxycholanate from example 1 as described above, 75 Kg of acetic acid 80%, were loaded into a reactor. The mixture was brought to the temperature of 30°-40° C. and about 750 Kg of sodium hypochlorite 15% were added. The mass was maintained at a temperature of 30°-40° C. for one hour, then the aqueous phase was separated and eliminated.

The organic phase was distilled until a paste-like residue was obtained, then 900 Kg of methyl alcohol were added and the mass was brought to between −5°/0° C. to obtain precipitation of the product, then the suspension was centrifuged and the residue washed with 300 Kg of methanol.

About 620 Kg of dry product were obtained. Return: 66.9% calculated on. 750 Kg of starting cholic acid.

The centrifugal mother liquors were conserved for use in the recovery step of the cholic acid as detailed below in example 8.

EXAMPLE 3

Step III—Preparation of Crude Chenodeoxycholic Acid

110 Kg of methyl 3α,7α-diacetoxy-12-ketocholanate (from example 2), 59 Kg of potassium hydroxide flakes, 220 Kg of triethyleneglycol and 112 Kg of hydrazine hydrate 80% were loaded into a reactor. The mass was heated to reflux (120-130° C.) for 1 hour, then the reaction mixture was subjected to distillation until a temperature of between 200°-210° C. was reached, which was maintained for 3 hours.

The reaction mass was transferred to another reactor containing 1300 Kg of water. The solution obtained was acidified by filtering or pouring 110 kilograms of sulphuric acid 34%. 1.00 Kg of chenodeoxycholic acid (primer) were then added.

The mass was brought to 65°-85° C. and maintained for 30 minutes. The suspension was then brought to 40°-50° C., centrifuged and the precipitate washed with 360 Kg of deionised water.

All the wet product obtained (crude chenodeoxycholic acid) was used in the subsequent step.

EXAMPLE 4

Step IV—Preparation of 3α-hydroxy-7-ketocholanic acid

144 Kg butyl alcohol, 112 Kg of methylene chloride, the entire chenodeoxycholic acid amount from example 3, 6.2 Kg of sulphuric acid 34% and 0.50 Kg of sodium bromide were loaded into a reactor. The mass was cooled to about 0° C. and, maintaining this temperature, a solution of 50.0 Kg of deionised water and 14.9 Kg of sodium bromate were added.

The mass was maintained at about 0° C. for 2 hours, then the mixture was heated at 55° C. until complete dissolution, the lower aqueous phase was separated and eliminated.

The organic phase was brought to dryness by distillation, then the following were added. 120 Kg of ethyl acetate. The suspension was then brought to 0° C. and centrifuged and the solid residue washed with 40.0 Kg of ethyl acetate.

About 75 Kg of 3α-hydroxy-7-ketocholanic acid were obtained.

Return: 88.1% calculated on 110 Kg of starting methyl 3α,7α-diacetoxy-12-ketocholanate used in step III (example 3).

EXAMPLE 5

Step V—Preparation of Ursodeoxycholic Acid Imidazole Salt

1095 Kg secondary butyl alcohol and 75 Kg of 3α-hydroxy-7-ketocholanic acid were loaded into a reactor. The mass was brought to reflux temperature then 77 Kg of metallic sodium were added in portions.

The mass was maintained at reflux for about 30 minutes, then 375 Kg of deionised water were added.

The mass was brought to a temperature of 65°-75° C., the aqueous phase was separated and eliminated.

150 Kg of deionised water and 26.0 Kg of phosphoric acid 85% were subsequently added. The mass was heated to around 30° C., the aqueous phase was separated and eliminated.

16.2 Kg of imidazole were added to the organic phase.

The secondary butyl alcohol was distilled until a dense yet stirrable residue was obtained, then 300 Kg of ethyl acetate and 75 Kg of deionised water were added. The mixture was heated to about 65° C., until complete dissolution, then brought to 30°-40° C. and stirred until self-priming with precipitation of the product.

The suspension was brought at a temperature of 5°-10° C., then centrifuged and the solid residue was washed with 37.5 Kg of deionised water and 55 Kg of ethyl acetate.

All the wet product obtained (ursodeoxycholic acid imidazole sal) was used in the subsequent step (example 6).

The intermediate thus obtained has the following known impurities content: "cheno" (less than 1.0%), "litho" (less than 0.05%), "cholic" (less than 0.1%) and "iso-urso" (less than 0.5%).

The centrifugal mother liquors were preserved and used in the example 9 for recovery of the 3α-hydroxy-7-ketocholanic acid.

EXAMPLE 6

Step VI—Preparation of Ursodeoxycholic Acid Methyl Ester

75 Kg of deionised water, the entire amount of ursodeoxycholic acid imidazole salt from example 6, 75 Kg of secondary butyl alcohol and 15.0 Kg of phosphoric acid 85% were loaded into a reactor. The mixture was heated (about 70° C.) until complete dissolution. The lower aqueous phase was separated and eliminated. The organic phase was brought to dryness by distillation, and the residue added or dissolved with 135 Kg of methyl alcohol and 1.50 Kg of hydrochloric acid 37%.

The mass was heated to reflux temperature and maintained for 2 hours, distilled to dryness and the residue was dissolved with 113 Kg of ethyl acetate.

The mass was cooled to 10°-15° C., then the suspension was centrifuged and the solid washed with 37.5 Kg of ethyl acetate.

All the wet product obtained (ursodeoxycholic acid methyl ester) was used in the subsequent step (example 7).

The centrifugal mother liquors were stored and used in example 9 for recovery of the 3α-hydroxy-7-ketocholanic acid.

EXAMPLE 7

Step VII—Preparation of Ursodeoxycholic Acid

135 Kg of deionised water, the entire amount of ursodeoxycholic acid methyl ester from example 7, 32.3 Kg of sodium hydroxide 30%, were loaded into a reactor. The mass was heated at reflux (about 97° C.) and maintained for 2 hours, then 300 Kg of deionised water were added.

The solution was brought to 60-65° C. then 113 Kg of ethyl acetate were added.

While maintaining the temperature between 60-65° C., a mixture of 16.2 Kg of acetic acid 80% and 16.2 Kg of phosphoric acid 85%, was filtered.

The suspension was stirred at 60°-65° C. for at least 15 minutes, then cooled to 20°-25° C. and stirred at this temperature for at least 30 minutes. The suspension was centrifuged and the solid washed with 37.5 Kg of ethyl acetate and 150 Kg of deionised water.

The product was dried at 80-90° C. and about 49.1 Kg of ursodeoxycholic acid, having the following impurity content, was obtained: "cheno" (less than 0.35%), "litho" (less than 0.05%), "cholic" (less than 0.1%) and "isourso" (less than 0.05%).

Return: 65.1% calculated on 75 Kg of starting 3α-hydroxy-7-ketocholanic acid used in step V (example 6).

EXAMPLE 8

Recovery of CHOLIC ACID from the centrifugal mother liquors from step I (example 1) and step II (example 2).

All the centrifugal mother liquors (ethyl acetate) originating from step I (example 1) were loaded into a reactor. The mixture was subjected to distillation until a dense residue was obtained, then all the centrifugal mother liquors (methanol) originating from step II (example 2) were added. The mixture was subjected to distillation, then at the temperature of about 20° C., a solution constituted by 20 Kg of deionised water, 0.23 Kg of sodium hydroxide 30% and 3.53 Kg of sodium borohydride was added.

The mass was kept at a temperature of about 20° C. for 2 hours, then heated to reflux and 450 Kg of sodium hydroxide 30% were added and the mass was maintained at reflux for 4 hours, then about 750 Kg of deionised water were added. 900 Kg of water-methyl alcohol mixture were distilled and then, at about 60° C., 375 Kg of ethyl acetate and 285 Kg of phosphoric acid 85% were added.

The aqueous phase was separated and eliminated, the organic phase was then cooled to about 5° C. to obtain the precipitation of cholic acid, which was centrifuged and washed with 113 Kg of ethyl acetate and 300 Kg of deionised water.

The product was dried and about 200 Kg of cholic acid were recovered. Return: 26.7% calculated on. 750 Kg of cholic acid used to start in example 1.

With this recovery, the actual balance of the first two steps of the process is as follows:
Kg of cholic acid actually consumed: 750−200=550 Kg
Kg of methyl 3α,7α-diacetoxy-12-ketocholanate obtained=620 Kg
Effective return of steps I and II: 91.3%

EXAMPLE 9

Recovery of the 3α-hydroxy-7-ketocholanic acid from the centrifugal mother liquors from steps V and VI (examples 5 and 6)

All the centrifugal mother liquors (ethyl acetate) from step VI (example 6) were loaded into a reactor and the solvent was distilled until a dry residue was obtained, which was dissolved with 45.0 Kg of deionised water and 5.3 Kg of sodium hydroxide 30%.

The mass was heated with direct steam (about 97° C.) to reflux and maintained for 1 hour, then all the centrifugal mother liquors from example 5 and 15.0 Kg of phosphoric acid 85% were added.

The lower aqueous phase was separated and eliminated. The organic phase was brought to dryness by distillation and the residue was dissolved with 37.5 Kg of secondary butyl alcohol, 30.0 Kg of methylene chloride, 1.5 Kg of sulphuric acid 34% and 0.15 Kg of sodium bromide.

The mixture was cooled to about 0° C. and, while maintaining it, a solution of 12 Kg of deionised water and 2.25 Kg of sodium bromate was filtered.

The mixture was maintained at approximately 0° C. for 2 hours, then 0.75 Kg of ammonia 30% were added and the mixture was heated at 55° C. until complete dissolution. The lower aqueous phase was separated and eliminated.

The organic phase was evaporated to dryness by distillation, then 45 Kg of ethyl acetate were added and the mixture was cooled to 20-30° C., then the suspension was centrifuged and the solid was washed with 15 Kg of ethyl acetate.

Around 20 Kg of recovery 3α-hydroxy-7-ketocholanic acid were obtained.

Return: 26.7% calculated on 75 Kg of starting 3α-hydroxy-7-ketocholanic acid used in step V (example 5).

With this recovery, the actual balance of the last four steps of the process is as follows:
Kg of 3α-hydroxy-7-ketocholanic acid actually consumed: 75−20=55 Kg
Kg of ursodeoxycholic acid (finished product of step VII, example 7) obtained=49.1 Kg
Actual return of these four steps: 88.7%

What is claimed is:

1. A process for the synthesis of ursodeoxycholic acid, said process comprising the following steps:
    (I) preparing methyl 3α,7α-diacetoxy-12α-hydroxycholanate through the esterification of cholic acid to obtain the methyl cholate intermediate which is not isolated and is acetylated in position 3 and 7 to obtain the methyl 3α,7α-diacetoxy-12α-hydroxycholanate intermediate which is isolated by crystallisation;
    (II) preparing methyl 3α,7α-diacetoxy-12-ketocholanate through oxidisation of the methyl 3α,7α-diacetoxy-12α-hydroxycholanate intermediate on the hydroxyl group in position 12 to give the methyl 3α,7α-diacetoxy-12-ketocholanate intermediate which is isolated by crystallisation;
    (III) preparing the crude chenodeoxycholic acid through Wolff-Kishner reduction of the ketone group in position 12 of the methyl 3α,7α-diacetoxy-12-ketocholanate intermediate, and reacting by means of hydrolysis the ester groups in position 3,7 and 24 to obtain the crude chenodeoxycholic acid;
    (IV) preparing the 3α-hydroxy-7-ketocholanic acid through oxidisation of the hydroxyl group in position 7 present on the crude chenodeoxycholic acid intermediate, to give 3α-hydroxy-7-ketocholanic acid;
    (V) preparing the ursodeoxycholic acid imidazole salt through reduction of the ketone group present in position 7 of the 3α-hydroxy-7-ketocholanic acid intermediate to give the crude ursodeoxycholic acid in the form of a mixture of ursodeoxycholic acid and chenodeoxycholic acid then treating with imidazole to give the ursodeoxycholic acid imidazole salt which is isolated by crystallisation;
    (VI) preparing the ursodeoxycholic acid methyl ester through esterification of the ursodeoxycholic acid imidazole salt intermediate to give the ursodeoxycholic acid methyl ester which is isolated by crystallisation;

(VII) preparing the ursodeoxycholic acid through hydrolysis of the ursodeoxycholic acid methyl ester intermediate, then acidifying to give the ursodeoxycholic acid.

2. The process according to claim 1, further comprising a recovery step (VIII) of the cholic acid, wherein the crystallisation mother liquors from steps (I) and (II) are stored and combined, are subjected to a recovery step of the cholic acid by means of a reduction reaction and subsequent basic treatment and acidification, to obtain a certain amount of recovered cholic acid corresponding to about 20-30% of the starting cholic acid used in step (I).

3. The process according to claim 2, wherein in step (VIII) the reduction is carried out using sodium borohydride in a basic environment.

4. The process according to claim 2 further comprising a recovery step (IX) of the 3α-hydroxy-7-ketocholanic acid, wherein the crystallisation mother liquors from steps (V) and (VI) are stored and the mother liquors from step (V), after distillation of the solvent, are subjected to a basic treatment then combined with the mother liquors from step (VI) to obtain a mixture that, after acidification, is subjected to oxidation in order to obtain a certain amount of 3α-hydroxy-7-ketocholanic acid corresponding to about 20-30% of the starting 3α-hydroxy-7-ketocholanic acid used in step (V).

5. The process according to claim 4, wherein in step (IX) the oxidation takes place by treating with sodium bromate in the presence of sodium bromide in an acid environment.

6. The process according to claim 1, wherein in step (I) the esterification reaction on the cholic acid takes place by means of methanol, catalysed by the hydrochloric acid and the acetylations in position 3 and 7 take place with acetic anhydride, in the presence of the 4-dimethylaminopyridine catalyst.

7. The process according to claim 1, wherein in step (II) the oxidation reaction takes by means of sodium hypochlorite.

8. The process according to claim 1, wherein in step (III) the reduction reaction is carried out in the presence of potassium hydrate and hydrazine, and the subsequent de-esterification reaction is carried out by means of treatment with sulphuric acid.

9. The process according to claim 1, wherein in step (IV) the oxidation reaction takes place by means of treatment with sodium bromate in the presence of sodium bromide in an acid environment.

10. The process according to claim 1, wherein in step (V) the ketone group reduction takes place by means of metallic sodium.

11. The process according to claim 1, wherein in step (VI) the esterification reaction of the ursodeoxycholic acid imidazole salt intermediate takes place after acidification of the imidazole salt with phosphoric acid and subsequent esterification by means of methanol in the presence of acid catalysis.

12. The process according to claim 1, wherein in step (VI) the hydrolysis reaction of the ursodeoxycholic acid methyl ester intermediate takes place by means of sodium hydrate and the subsequent acidification takes place with acetic acid and phosphoric acid.

* * * * *